United States Patent [19]

Hufnagle

[11] Patent Number: 4,635,633
[45] Date of Patent: Jan. 13, 1987

[54] COMBINATION STERILE PAD SUPPORT AND LANCET

[76] Inventor: Douglas R. Hufnagle, 75 Executive Dr., Westerville, Ohio 43081

[21] Appl. No.: 682,519

[22] Filed: Dec. 17, 1984

[51] Int. Cl.$^4$ .............................................. A61B 17/34
[52] U.S. Cl. .................................. 128/314; 128/329 R
[58] Field of Search .............. 128/314, 329 R, 334 R; 604/192, 199, 218, 1, 3

[56] References Cited

U.S. PATENT DOCUMENTS

| | | | |
|---|---|---|---|
| 2,117,469 | 5/1938 | Woodyatt | 604/199 |
| 2,627,269 | 2/1953 | McGregor | 604/2 |
| 2,642,065 | 6/1953 | Negri | 604/3 |
| 2,851,036 | 9/1958 | Lipari | 604/192 |
| 3,221,739 | 12/1965 | Rosenthal | 128/329 |
| 3,358,689 | 12/1967 | Higgins | 128/329 R |
| 3,680,559 | 8/1972 | Gorbahn | 604/218 |
| 4,243,035 | 1/1981 | Barrett | 604/1 |
| 4,375,815 | 3/1983 | Burns | 128/329 R |

Primary Examiner—Gene Mancene
Assistant Examiner—David I. Tarnoff
Attorney, Agent, or Firm—John L. Gray

[57] ABSTRACT

In order for diabetics to test themselves for stat glucose levels to determine whether or not they should self administer insulin, it is necessary to draw a drop of blood from the diabetic's finger, place the drop of blood on a commercially available blood glucose test media and compare the resulting color of the test strip with a standard chart to determine the blood glucose concentration. This invention is directed to a cheap, disposable, combination sterile pad support and lancet which may be used to disinfect the end of the finger area and then used to stick the finger to draw blood and the sterile pad may also be held on the stick site firmly, thus aiding the blood clotting time after the drop of blood has been placed on the blood glucose test strip.

7 Claims, 6 Drawing Figures

COMBINATION STERILE PAD SUPPORT AND LANCET

BACKGROUND OF THE INVENTION

Some diabetics must test themselves for stat glucose levels up to four times a day in order to determine whether or not they should self-administer insulin. The procedure involves drawing a drop of blood from the diabetic's finger, placing the drop of blood on a commercially available blood glucose test strip, and comparing the resulting color of the test strip with a standard chart to determine the blood glucose concentration. It is important that the end of the finger site area be cleaned properly prior to puncturing the skin to avoid contamination because diabetics are more prone to infection and do not heal as quickly as the average members of the population. Consequently, it is necessary for the diabetic to first clean the site area at the end of the finger with an antiseptic and then insert a sharp lancet into the finger so that the drop of blood will be released.

While the use of alcohol in pint or quart bottles combined with cotton balls for cleaning the site area is feasible in a home environment, it is impractical for the diabetic who is at work, school, or traveling. Some diabetics have improvised by carrying separate lancets and prepackaged, sealed, alcohol swabs that are designed for large macro cleaning areas to prepare for hypodermic needle injections. Examples of such prepackaged alcohol swabs are shown in U.S. Pat. No. 3,542,634, Such, et al, and an integral lancet and holder is shown in U.S. Pat. No. 3,358,689, Higgins. The disadvantage of using this system is that the prepackaged alcohol swab contains much more alcohol than is required for a finger stick procedure to draw a drop of blood and because these are two separate items, sometimes the diabetic will have the swabs and not the lancet and sometimes the diabetic will find that he has the lancet and not the swab when he is away from home.

Combination packages containing alcohol swabs for macro cleaning for hypodermic needle injection in combination with hypodermic needles are available as exemplified by U.S. Pat. No. 2,117,469, Woodyat, and U.S. Pat. No. 2,851,036, Lipari and U.S. Pat. No. 2,707,743, Gingras. Such devices, of course, are designed for the injection of medication into the body and their use to draw a drop of blood and then be discarded would result in a prohibitively expensive cost to the user.

SUMMARY OF THE INVENTION

This invention is directed to a cheap, disposable, combination sterile pad support and lancet which may be used to disinfect the end of the finger area and then used to stick the finger to draw blood and the pad may also be held on the stick site firmly, thus aiding the blood clotting time after the drop of blood has been placed on the blood glucose test strip.

It is therefore an object of this invention to provide a small compact, sterile pad support in combination with a protected sterile lancet.

It is an additional object of this invention to provide such a device wherein the pad is mechanically secured within the device and in which the lancet is either cast as an integral part of the device or which may be frictionally retained in the unit.

It is a further object of this invention to provide such a device which may be readily gripped by an individual in performing the procedures contemplated.

These, together with other objects and advantages of the invention should become apparent in the details of construction and operation as more fully described hereinafter and claimed, reference being had to the accompanying drawings forming a part hereof wherein like numerals refer to like parts throughout.

DETAILED DESCRIPTION OF THE INVENTION

Figure 1:
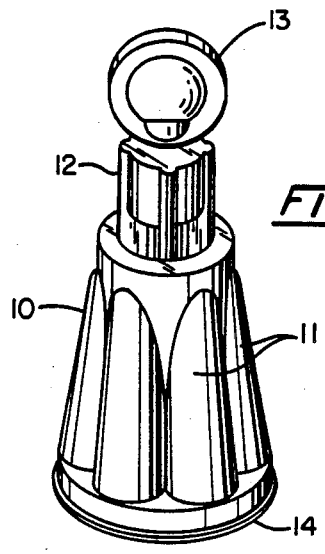
FIG. 1 is a perspective view of the combination sterile pad support and lancet.

Referring now more particularly to FIG. 1, the support member 10 is shown provided with a plurality of upstanding finger engaging portions 11—11 providing a good grip for the user. Inserted in support member 10 and frictionally held therein is a lancet 12 such as that shown in U.S. Pat. No. 3,358,689, Higgins. However, it should be understood that the lancet may be cast as an integral part of support member 10. Lancet 12 is provided with a protective cover 13 and a heat sealable foil 14 covers the base of the support member 10 thus preventing the antiseptic in the antiseptic impregnated absorbent pad in support member 10 from evaporating.

Figure 2:
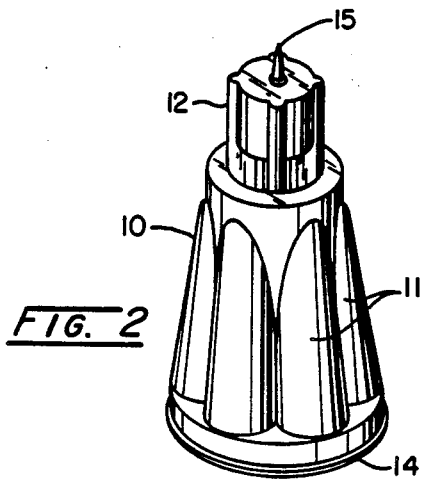
FIG. 2 is the same perspective view with the protective cover on the lancet removed.

Referring now more particularly to FIG. 2, the protective cover 13 has been removed revealing the pointed end 15 of the lancet 12.

Figure 3:
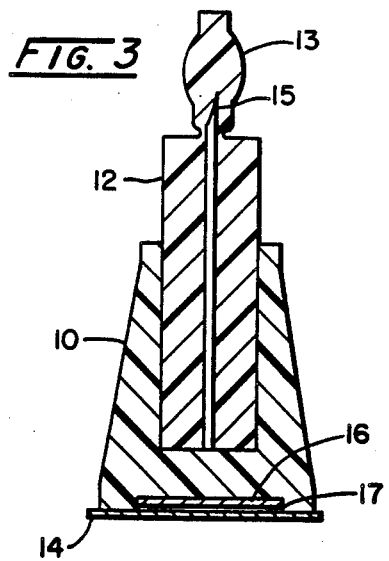
FIG. 3 is a sectional view of the combination sterile pad support and lancet shown in FIG. 1.

Referring now more particularly to FIG. 3, the antiseptic impregnated absorbent pad 16 is shown held in place by the reverse bevel portion 17 of the recessed portion of support member 10.

Figure 4:
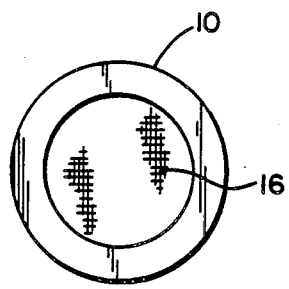
FIG. 4 is an end view of FIG. 3 with the protective cover on the sterile pad removed.

Referring now more particularly to FIG. 4, the end view of support member 10 is shown with foil 14 removed showing the antiseptic impregnated absorbent pad 16. The pad 16 is of a size so that it will adequately clean and fit the end of a person's finger. It is preferably impregnated with a small amount of 70 percent isopropyl alcohol. The pad 16 is held in place by means of the reverse bevel 17 in the base of support member 10 and thus requires no mechanical or adhesive fasteners. The heat sealable foil 14 is heat sealed to the base of support member 10 around the periphery of it base, thus preventing the alcohol in pad 16 from evaporating and may be readily removed by peeling it off when the user is ready to prepare the site for finger stick. Support member 10 is preferably made from injected low density polystyrene.

Figure 6:
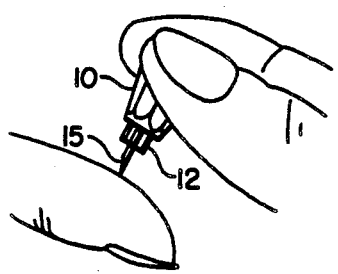
FIG. 6 shows the lancet being inserted in the stick site.
Figure 5:
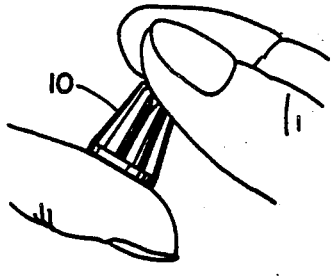
FIG. 5 shows the use of the device in preparing the site for the stick procedure and also showing the use of the device after the blood has been removed to aid blood clotting.

Referring now more particularly to FIG. 5, the combination sterile pad support and lancet is shown with the foil cover removed and with the alcohol impregnated pad 16 in contact with the finger end thus disinfecting the area which will receive the lancet. The protective cover 13 is then twisted off and discarded leaving the sharp pointed end 15 of the lancet 12 exposed and the position of the device is reversed as shown in FIG. 6 so that the sharp pointed end 15 of the lancet 12 may be inserted in the finger or the lancet 12 may be removed from the support 10 and used in conjunction with a mechanical device to puncture the skin. After the drop of blood has been removed and placed on the blood glucose test strip, the support member 10 may be placed with the pad 16 in firm contact with the stick site, as in FIG. 5, thus aiding the blood clotting time.

By combining the sterile pad support and the lancet in a single unitary device, the diabetic patient always has these two necessary preparation products together and since both the pad 16 and the sharp end 15 of the lancet 12 are protected and are in a sterile condition, a user may safely carry these in a purse or pocket without contamination so that they may be used and then safely discarded.

While this invention has been described in its preferred embodiment, it is appreciated that variations thereon may be made without departing from the proper scope and spirit of the invention.

What is claimed is:

1. A combination sterile pad support and lancet comprising a member in the shape of the frustum of a cone containing a hollow cylinder extending along the axis of said cone and coaxial therewith, and one end of said cylinder terminating adjacent to, but spaced from, the base of said cone, the opposite end of said cylinder terminating in the top of the frustum of said cone, said cylinder being of a size and shape adapted frictionally to hold a conventional lancet, said lancet being positioned in said cylinder, said member provided with a centrally positioned recess in the base of said member, the depth of said recess being substantially less than the width of said recess, and absorbent pad in said recess containing an antiseptic fluid, said pad having a shape complementary to said recess and substantially filling said recess, said recess being deep enough to hold a quantity of said antiseptic fluid in addition to that antiseptic fluid which saturates said pad, a removable cover on said base completely covering said pad and adapted to cooperate with said recess to prevent said antiseptic from coming in contact with the atmosphere, said cover being separable from said pad whereby said pad will remain in said recess when said cover is removed from said base, a sharp lancet tip extending from the top of said conically-shaped member and a removable cover on said sharp lancet tip.

2. The combination sterile pad support and lancet of claim 1 wherein said conically-shaped member is provided with upstanding finger engaging portions on its outer surface.

3. The combination sterile pad support and lancet of claim 1 wherein said antiseptic is isopropyl alcohol.

4. The combination sterile pad support and lancet of claim 1 wherein said removable cover on said base member is a foil, heat sealed to said base.

5. The combination sterile pad support and lancet of claim 1 wherein said lancet is frictionally held within said conically-shaped member.

6. The combination sterile pad support and lancet of claim 1 wherein said removable cover on said sharp lancet tip is molded into the remainer of the lancet structure.

7. The combination sterile pad support and lancet of claim 1 wherein the diameter of the inner portion of said centrally positioned recess is greater than the diameter of said recess adjacent the surface of the base of said conically-shaped member.

* * * * *